US008557192B2

(12) United States Patent
Thorhauge

(10) Patent No.: US 8,557,192 B2
(45) Date of Patent: Oct. 15, 2013

(54) METHOD AND REACTOR FOR THE PREPARATION OF METHANOL

(75) Inventor: Max Thorhauge, Herlev (DK)

(73) Assignee: Haldor Topsoe A/S, Lyngby (DK)

(*) Notice: Subject to any disclaimer, the term of this patent is extended or adjusted under 35 U.S.C. 154(b) by 0 days.

(21) Appl. No.: 13/524,910

(22) Filed: Jun. 15, 2012

(65) Prior Publication Data
US 2012/0269697 A1  Oct. 25, 2012

Related U.S. Application Data

(62) Division of application No. 12/812,480, filed as application No. PCT/EP2009/000974 on Feb. 12, 2009, now Pat. No. 8,202,915.

(30) Foreign Application Priority Data

Feb. 25, 2008  (DK) .................................. 2008 00260

(51) Int. Cl.
| F28D 7/00 | (2006.01) |
| B01J 19/00 | (2006.01) |
| B01J 8/00 | (2006.01) |
| B01J 8/02 | (2006.01) |
| B01J 8/04 | (2006.01) |
| B01J 35/02 | (2006.01) |
| C07C 27/00 | (2006.01) |
| C07C 27/06 | (2006.01) |

(52) U.S. Cl.
USPC ........... 422/200; 422/129; 422/187; 422/198; 422/211; 422/600; 422/630; 518/706; 518/707; 518/708

(58) Field of Classification Search
USPC ......... 422/129, 187, 198, 211, 600, 630, 200; 585/310, 315; 518/706–708
See application file for complete search history.

(56) References Cited

U.S. PATENT DOCUMENTS

| 3,970,435 A * | 7/1976 | Schultz et al. ..................... 48/61 |
| 4,734,264 A * | 3/1988 | Vollhardt et al. .............. 422/148 |
| 5,861,353 A * | 1/1999 | Viola et al. ..................... 502/225 |
| 6,218,439 B1 * | 4/2001 | Kobayashi et al. ........... 518/713 |
| 7,144,923 B2 * | 12/2006 | Fitzpatrick ..................... 518/706 |
| 2003/0068260 A1 | 4/2003 | Wellington et al. |
| 2007/0122322 A1 * | 5/2007 | Te Raa et al. ................. 422/197 |

FOREIGN PATENT DOCUMENTS

| EP | 0 737 646 A2 | 10/1996 |
| GB | 1 565 824 A | 4/1980 |
| WO | WO-98/04342 A1 | 2/1998 |

* cited by examiner

*Primary Examiner* — Walter D Griffin
*Assistant Examiner* — Natasha Young
(74) *Attorney, Agent, or Firm* — Dickstein Shapiro LLP

(57) ABSTRACT

Improved design of a catalytic method and reactor for the production of methanol at equilibrium conditions, whereby methanol, as it is formed, is separated from the gaseous phase into the liquid phase within the reactor without reducing the catalytic activity of the methanol catalyst. This is achieved by adjusting the boiling point or temperature of a liquid cooling agent being in indirect contact with the catalyst particles and by providing a specific ratio of catalyst bed volume to cooling surface area. Thereby, condensation of methanol as it is formed in the gaseous phase takes place for the most at the cooling surface arranged evenly distributed within the reactor and if at all within a very limited region of the catalyst bed.

4 Claims, 11 Drawing Sheets

METHOD AND REACTOR FOR THE PREPARATION OF METHANOL

Figure 1A:
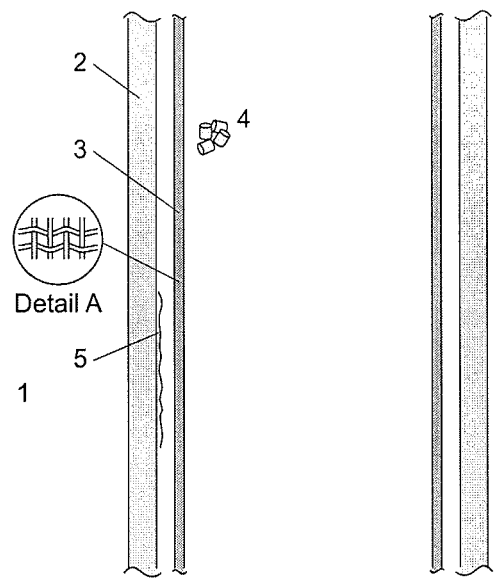

This is a divisional of application Ser. No. 12/812,480 filed Jul. 12, 2010, now U.S. Pat. No. 8,202,915 which is a 371 of PCT/EP2009/000974 filed Feb. 12, 2009.

FIELD OF INVENTION

The present invention relates to the industrial production of methanol by conversion of a synthesis gas containing hydrogen, carbon monoxide and carbon dioxide in the presence of a methanol synthesis catalyst.

The invention is in particular a method and a reactor for improving methanol production with respect to equilibrium limitation, and thereby reducing or eliminating synthesis gas recirculation by in situ separation of methanol as it is produced from the synthesis gas.

BACKGROUND OF THE INVENTION

The preparation of methanol is based on following three equilibrium reactions:

$$CO + 2H_2 \Longleftrightarrow CH_3OH \quad (1)$$

$$CO_2 + 3H_2 \Longleftrightarrow CH_3OH + H_2O \quad (2)$$

$$CO + H_2O \Longleftrightarrow CO_2 + H_2 \quad (3)$$

Due to the equilibrium only a fraction of the synthesis gas is converted to methanol and the remaining part of the synthesis gas has to be recycled. In situ separation of methanol from the synthesis gas is disclosed in U.S. Pat. No. 4,731,387. In a gas solid trickle flow reactor the methanol is removed by an absorption material and thereby the equilibrium condition improves. After having passed the reactor the methanol is desorbed from the absorption material and the absorption material is recycled to the inlet of the reactor. The drawbacks of such system lie in the complexity of the system, which results in operational difficulties and a higher investment cost.

Another way of overcoming the equilibrium limitations is disclosed in U.S. Pat. No. 5,262,443, where the catalytic reactor is operated at a temperature and pressure where a part of the produced methanol condensates in the catalytic bed. By applying this invention, it is possible to reduce of eliminate the expensive synthesis gas recycle. There are, however, two drawbacks by operating in this way.

In order to operate below the gas dew point, the catalyst temperature has to be reduced below the optimal temperature level for the catalytic reaction. The lower temperature results in a lower activity, which increases the necessary catalyst volume and cost of the reactor.

The second problem involves the condensation of methanol in the porous catalyst. The synthesis gas has to diffuse inside the catalyst through the pore system to initiate the catalytic reaction. If the pores are filled with methanol, the diffusion rate and catalytic activity are severely reduced.

These two problems reduce the catalyst activity several times compared to the activity obtained in the conventional methanol synthesis process. As a consequence of the reduced activity the condensing reactor has to be increased in size resulting in reactors being more expensive than conventional reactors with recycle of synthesis gas.

SUMMARY OF THE INVENTION

The present invention provides in general an improved design of a catalytic method and reactor for the production of methanol at equilibrium conditions, whereby methanol as it is formed is separated from the gaseous phase into the liquid phase within the reactor, without reducing the catalytic activity of the methanol catalyst. This is achieved by adjusting the temperature of a liquid cooling agent being in indirect contact with the catalyst particles and by providing a specific ratio of catalyst bed volume to cooling surface area. Thereby, condensation of methanol as it is formed in the gaseous phase takes place for the most at the cooling surface arranged evenly distributed within the reactor and if at all within a very limited region of the catalyst bed.

More particularly, the invention provides a method for the preparation of methanol comprising the steps of reacting a synthesis gas containing hydrogen, carbon monoxide and carbon dioxide in a fixed bed reactor of methanol synthesis catalyst particles being indirectly cooled with a cooling agent, and condensing methanol as it is formed on a cooling surface by adjusting pressure of the cooling agent to obtain a boiling point (TBW) of the cooling agent between 60° C. and 170° C., and maintaining the catalyst temperature above dew point of the methanol by adjusting area of the cooling surface (ACOOL) at the boiling point of the cooling agent in such way that the ratio of settled catalyst bulk volume (VCAT) to the cooling surface area (ACOOL) is between 0.0125 m and 0.125 m. A further method of the invention for the preparation of methanol comprises the steps of reacting a synthesis gas with hydrogen, carbon monoxide and carbon dioxide in a fixed bed reactor of methanol synthesis catalyst particles being indirectly cooled with a cooling agent, and condensing methanol as it is prepared on a cooling surface by adjusting pressure of the cooling agent to provide a boiling point (TBW) of the cooling agent between 60° C. and 170° C., and maintaining the catalyst temperature above dew point of the methanol by adjusting area of the cooling surface (ACOOL) in such way that ratio (Z) of settled catalyst bulk volume to product of area of the cooling surface (ACCOL) and equivalent diameter of the catalyst (DEQ) is between 2.0 and 30, where the equivalent diameter of the catalyst is calculated by means of the following equations:

$DEQ_1 = (6*(\text{volume of a particle of the methanol synthesis catalyst}[m^3]/3.14)^{0.33}$ with catalyst particles of the same size, or

$DEQ_2 = (\Sigma\, w(i)*(DEQ(i)^3))^{0.33}$, where w(i) is the weight fraction of catalyst particles with an equivalent diameter of DEQ(i)[m].

In a preferred embodiment of the invention, temperature of the methanol catalyst particles is maintained above the dew point of the methanol by a heating agent including pressurized water with a boiling point between 220° C. and 280° C., steam with a dew point between 220° C. and 280° C. or a mixture thereof, the heating agent being passed through an internal heating means having a surface area so that ratio of the surface of heating means to the surface of the cooling area (ACOOL) is between 0.3 and 3.0.

Further embodiments of the inventive method are described below.

The invention provides in addition a methanol reactor being useful in the method according to the invention.

In one aspect of the invention, a methanol reactor comprises within a common shell a fixed bed of methanol catalyst particles and cooling means adapted to indirectly cooling a methanol synthesis gas with a cooling agent, wherein ratio of settled catalyst bulk volume to cooling surface area (VCAT/

ACOOL) of the cooling means is between 0.0125 m and 0.125 m at a boiling point of the cooling agent of between 60° C. and 170° C.

In further an aspect of the invention, a methanol reactor comprises within a common shell a fixed bed of a methanol catalyst and cooling means adapted to indirectly cooling a methanol synthesis gas with a cooling agent, wherein ratio (Z) of catalyst bulk volume to multiplication product of area of the cooling surface with equivalent diameter of the catalyst (DEQ) is between 2.0 and 30 at a boiling point of the cooling agent of between 60° C. and 170° C., where the equivalent diameter of the catalyst is calculated by means of the following equation:

$$DEQ_1 = (6*(\text{volume of a particle of the methanol synthesis catalyst}[m^3]/3.14)^{0.33} \text{ with catalyst particles of the same size and with catalyst particles of different size by means of the following equation:}$$

$$DEQ_2 = (\Sigma w(i)*(DEQ(i)^3))^{0.33},$$

where w(i) is the weight fraction of catalyst particles with an equivalent diameter of DEQ(i) [m].

A preferred embodiment of the above described inventive reactors comprises furthermore within the common shell heating means adapted to indirectly maintaining temperature of the methanol catalyst above the dew point of the methanol with a heating agent, wherein surface ratio of the surface of the heating means to the cooling means is between 0.3 and 3.0.

Further embodiments of the invention are described below.

DETAILED DESCRIPTION OF THE INVENTION

In general, the type of reactor for use in the invention is of minor importance. The required boiling point or temperature of the liquid cooling agent will be the same for any of the reactor types and the catalyst volume to cooling surface area will be identical. Most useful methanol reactors are reactors cooled either by rising vapour or by heating a pressurized liquid cooling agent.

The "temperature" of the liquid cooling agent is the average temperature defined as the cooling agent temperature after having received half of the total transferred heat.

The three principal methanol reactor types are:

Reactor type 1, where synthesis gas enters at the top of the catalytic bed and the catalyst bed is indirectly surrounded by the liquid cooling agent and the synthesis gas and condensed liquid methanol moves concurrently downwards. An example of such a reactor is shown in the drawings in FIG. 8.

Figure 9:
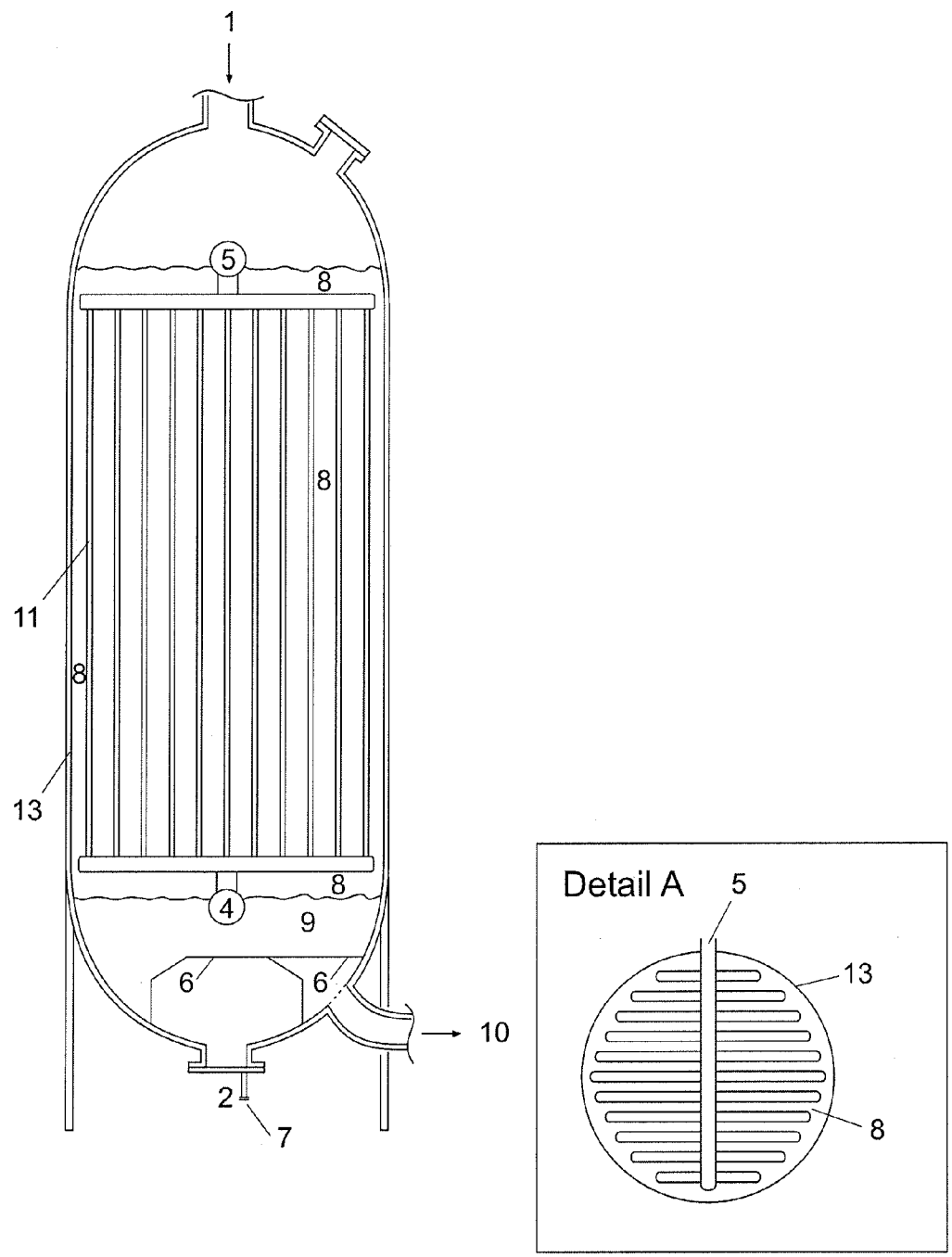

Reactor type 2, where synthesis gas enters at the top of the catalytic bed and the liquid cooling agent is indirectly surrounded by a catalyst bed, and the synthesis gas and condensed liquid moves concurrently downwards. An example of such a reactor is shown in FIG. 9.

Figure 11:
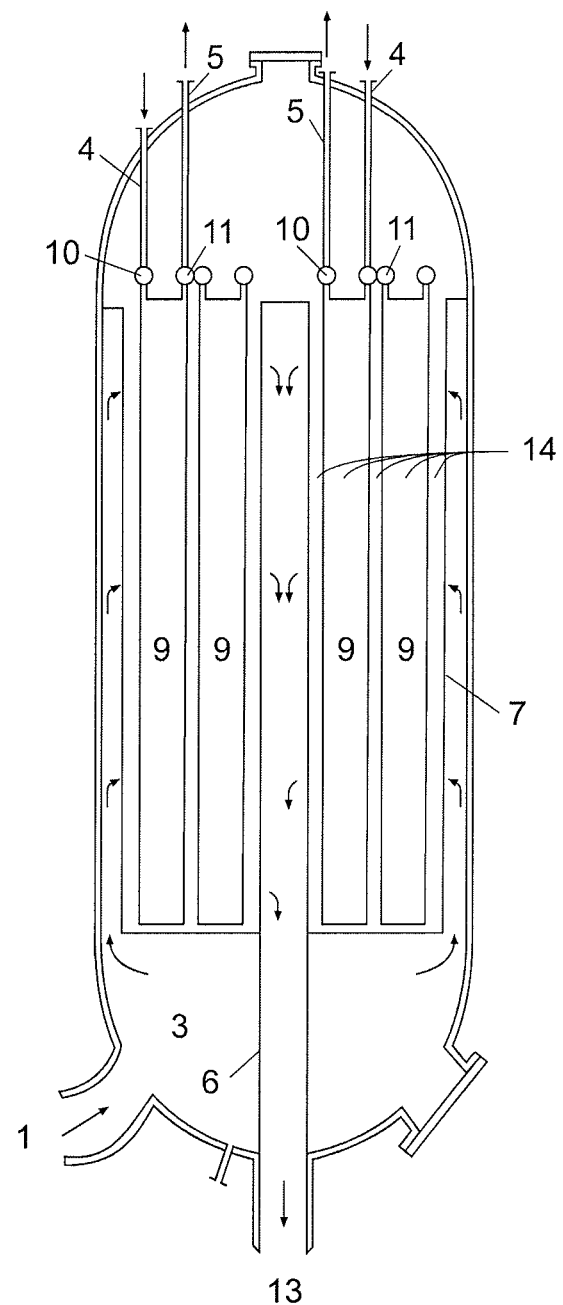

Reactor type 3, where synthesis gas enters perpendicular to the cylindrical reactor axis and the liquid cooling agent is indirectly surrounded by a catalyst bed and the synthesis gas and condensed liquid methanol pass in radial manner through the reactor. An example of such a reactor is shown in FIG. 11.

The term "indirectly surrounded" mentioned hereinbefore and in the following refers to the commonly known principle of indirect heat exchange, wherein a cooling or heating agent is in indirect heat contact with another fluid being separated form the cooling/heating agent by a heat transferring surface in form of e.g. a wall of a tube or a plate of a heat exchanger.

In order to obtain condensation of methanol as it is formed in the catalyst bed takes place substantially at a cooling surface in accordance with the invention two contradicting measures have to be fulfilled:

1. To have a sufficiently high temperature in the catalyst bed, the thermal flux has to be small. This can be achieved by decreasing the cooling area or increasing the temperature of the cooling agent.

2. A sufficiently high temperature requires a high heat production or a high reaction rate. If methanol synthesis gas is at thermodynamic equilibrium with methanol the catalytic reaction will come to a stand still, and hence the heat production will vanish. It is, therefore, necessary to ensure that the produced methanol is transported to the cooling surface at a high rate. This can be achieved by increasing the cooling area or decreasing the temperature of the liquid cooling agent.

By the invention, the catalytic activity is kept high by avoiding condensation through adjustment of the ratio between the catalyst volume and the cooling surface area, together with a specific temperature of the liquid cooling agent as described in detail below.

The length of transport path of methanol being produced in the catalyst bed is adjusted to a length at which the methanol concentration in the catalytic bed is suitable low that the heat of reaction increases to a temperature, where it compensates for the amount of heat removed by the same transport length. At the same time ensures the temperature of cooling surface that the temperature is sufficiently low that condensation takes place, and the catalytic bed temperature is so high that condensation on the catalyst is avoided and a high reaction rate is maintained.

This effect is achievable at a specific temperature of the cooling surface. The heat that needs to be removed from the reactor is of such a magnitude that for any practical reason it can only be removed by evaporation heat or by heating a liquid cooling agent. The surface temperature of the cooling area is close to that of the temperature of the liquid cooling agent.

In order to avoid condensation of methanol in the catalyst bed, the heat of production must be sufficiently high to compensate for the heat removed on the cooling area by increasing the ratio of catalyst volume to cooling surface area and the ratio of catalyst volume to cooling surface area must be adequate to the transport of the produced methanol vapour to the cooling surface.

It is preferred that re-entrainment of liquid methanol is substantially reduced or avoided. Liquid re-entrainment may be avoided by reducing the flow resistance of the downwards flowing raw methanol on the cooling surface. This is realized by employing catalyst particles with an equivalent diameter, of more than 0.002 m. Liquid re-entrainment may be further reduced by means of a liquid film stabilizer as shown in FIGS. 1-7.

Liquid methanol re-entrainment into the catalyst bed may also be avoided by introducing a heating area into the reactor that maintains temperature of the catalyst bed above the dew point of methanol. The heating area will also keep the catalyst temperature above the dew point in cases where the heat production is low as with high module gases, and near the outlet of the catalyst bed. The heating area shall, as for cooling area, be evenly distributed within the catalyst bed in order to obtain a forced temperature gradient in the bed. Since the heat production is higher at the synthesis gas inlet of the reactor as compared with outlet of the reactor, the heating area may cool near the inlet region of the reactor and solely heat the catalyst bed in the near outlet region of the reactor. It is preferred to introduce the cooling agent in a co-current flow direction with the synthesis gas. Thereby, the outlet region of the reactor can be reheated by excess heat from inlet region of the reactor. The heating agent for use in the heating area is preferably boiler feed water, steam or a mixture of these. The pressure of the heating agent is preferably between about 1.2 MPa and about 6.4 MPa.

The main advantage of the method and rector of this invention is a high conversion of methanol synthesis gas in the reactor obtained by a continuous removal of the formed methanol from the gaseous phase into the liquid phase on a cooling surface through condensation. A result, the methanol process can be carried out in the once through mode without recirculation of unconverted synthesis gas.

Compared with conventional boiling water methanol reactor, an advantage of the present invention is an increased steam production, since the heat of condensation is utilized in the reactor for steam production, whereas the condensation heat typically is removed in a subsequent cooling water condenser.

If the reaction heat is removed by heating boiler feed water, the boiler feed water can subsequently be cooled by flashing of the formed steam in an external flash drum.

As in the conventional methanol process some by-products are formed, among these are acetone and methyl ethyl ketone, which are difficult to remove by distillation. Since the hydrogenation reaction is very fast, the ketones will be in thermodynamic equilibrium at the given temperature in the reactor. The ketones will mainly be dissolved in the condensed raw methanol at the cooling surface, where the thermodynamic equilibrium is more favourable toward the conversion of the ketones to the corresponding alcohols. This results in a lower ketone content in the produced methanol compared to a conventionally operated methanol reactor.

The above described process parameters and reactor design and dimensions can be adjusted by means of the following procedure:

In order to obtain condensation of the formed methanol on the cooling surface, the temperature of the cooling agent has to be below the dew point of the methanol. If the reaction heat is removed by evaporation of the liquid cooling agent, the pressure of the liquid cooling agent has to be adjusted to provide a boiling point (TBW) of the cooling agent between 60° C. and 170° C. If the reaction heat is removed by heating a liquid coolant, the average temperature of the liquid coolant (TBW) must be between 20° C. and 170° C. TBW is the average cooling agent temperature. The average temperature is defined as the cooling agent temperature after having received half of the total transferred heat. For vapour rising reactors the average temperature will be close to the boiling point of the liquid cooling agent. The absolute pressure of the synthesis gas at reactor inlet must be above 8.5 MPa.

Having determined the average temperature of the liquid cooling agent, the ratio of catalyst volume to cooling surface area has to be adjusted. In order to avoid condensation of methanol in the catalyst bed, the heat of production must be sufficiently high to compensate for the heat removed on the cooling area by increasing the ratio of catalyst volume to cooling surface area and the ratio of catalyst volume to cooling surface area must be adequate to the transport of the produced methanol vapour to the cooling surface. Both conditions can be achieved by adjusting area of the cooling surface (ACOOL) in such way that the ratio of settled catalyst bulk volume (VCAT) to the cooling surface area (ACOOL) is between 0.0125 m and 0.125 m. In further an embodiment of the invention the area of the cooling surface (ACOOL) is adjusted in such a way that ratio (Z) of settled catalyst bulk volume to multiplication product of area of the cooling surface (ACCOL) and equivalent diameter of the catalyst (DEQ) is between 2.0 and 30.

where:

DEQ[m] is the equivalent diameter of the catalyst pellet calculated as the diameter of a sphere having the same volume as the catalyst particle DEQ=$(6*(\text{volume of particle } [m^3])/3.14)^{0.33}$. If more than one pellet size are employed a weight average equivalent diameter is calculated DEQ=$(\Sigma w(i)*(DEQ(i))^3)^{0.33}$ where w(i) is the weight fraction of particles with an equivalent diameter of DEQ(i)[m];

VCAT[$m^3$] is the settled bulk volume of the catalyst in the reactor; and

ACOOL[$m^2$] is a heat transfer area of the cooling surface where condensation of methanol takes place.

For reactor type 1, ACOOL is the total inner area of the catalyst tubes. If the catalyst tubes have longitudinal inner fins, ACOOL is the outer area of the largest cylinders enclosed by the finned tubes. For reactor types 2 and 3, ACOOL is the total outer area of the cooling tubes containing the liquid cooling agent with a temperature of TBW. If the catalyst tubes have longitudinal fins, ACOOL is the outer area of the smallest cylinders enclosing the finned tubes.

If plate heat exchangers are employed, ACOOL is the total outer area of the smallest rectangular enclosing the heat exchange plates.

If liquid re-entrainment into the catalyst bed takes place or if the synthesis gas inlet module M is above 3 where:

$$M = (Y(H_2) - Y(CO_2))/(Y(C0) + Y(CO_2))$$

(M is the inlet gas module, Y is the molar fraction)

it is preferred to introduce a second heating area AREHEAT [$m^2$] into reactor types 2 and 3 as defined previously. This second heating area will ensure that the catalyst temperature is maintained above the dew point of methanol. The heating agent used in the heating area can be a liquid media, vapour or a mixture of these with a boiling point of between 220° C. and 280° C. for the liquid media or a dew point between 220° C. and 280° C. for the vapour.

DETAILED. DESCRIPTION OF THE FIGURES

Figure 1B:
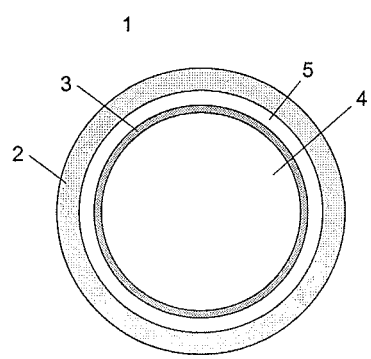

FIGS. 1A and 1B show wire mesh internal equipment for use in the invention. A liquid cooling media 1 is on the outside of a steel tube 2. Cooling tube is on its inner wall provided with a cylindrical wire mesh 3 (detail A) spaced apart from the wall. Tube 2 holds a fixed catalyst bed 4. A condensate film 5 of methanol being produced inside bed 4 in the gaseous phase condensates as film on the inner tube wall and flows downwards between the inner wall and the wire gauze. The arrangement can be reversed in such manner that a cooling agent is inside the tube and the wire gauze cylinder outside the tube and the catalyst bed outside the wire gauze cylinder.

Figure 2:
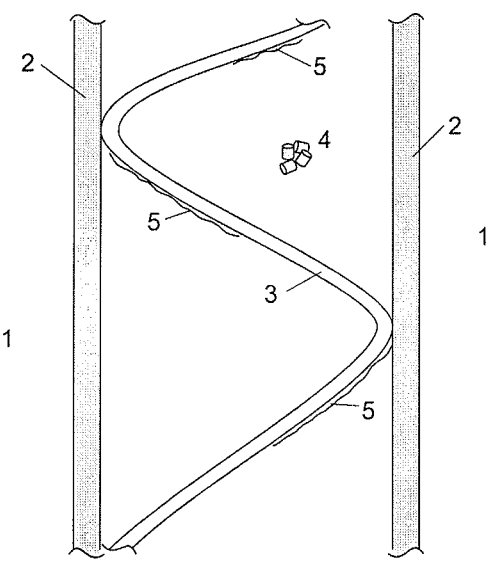

FIG. 2 is steel spiral internal equipment for use in the invention. A liquid cooling agent 1 is on the outside of a steel tube 2. Steel spiral 3 is arranged within tube 2 holding a fixed catalyst bed 4. Methanol condensate film 5 is flowing downwards on the lower side of the spiral.

Figure 3:
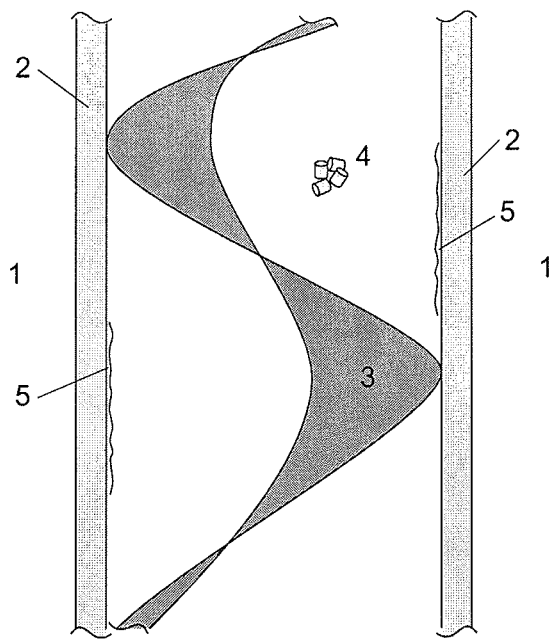

FIG. 3 shows steel helix internal equipment for use in the invention. A liquid cooling 1 is outside 1 of a steel tube 2. A steel helix 3 is arranged within a fixed catalyst bed 4. A methanol condensate film 5 flowing downwards on the inner wall tube 2 and is forced to wall 2 due to the centrifugal force created by the forced rotation of a synthesis gas passing in axial direction through tube 2. Tube 2 can be equipped with two helixes 3 each spiral displaced 180° to each other.

Figure 4A:
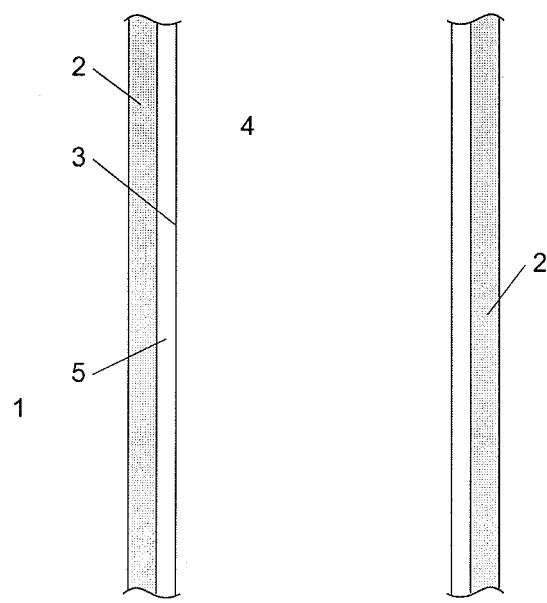
Figure 4B:
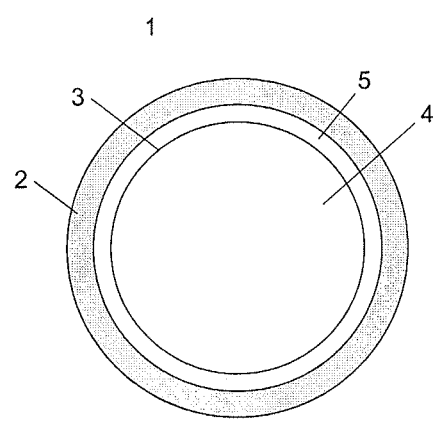

FIGS. 4A and 4B show porous fibre internal equipment for use in the invention. A liquid cooling agent surrounds a cooling tube 2 being equipped with a woven fibre cylinder 3 or a ceramic bonded fibre mat cylinder on inner wall of tube 2. A fixed catalyst bed 4 is arranged within tube 2. A methanol condensate film 5 flows downwards inside the porous fibre internal equipment. The arrangement can be reversed in such manner that the cooling agent is inside tube 2, and equipment 3 is outside the tube and the catalyst bed 4 outside equipment 3.

Figure 5:
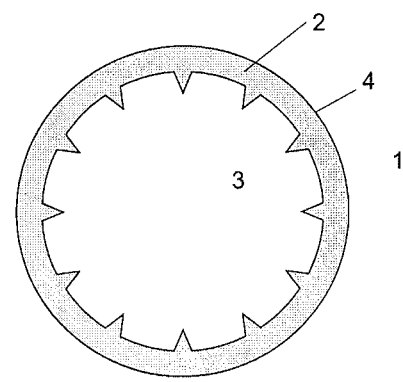

FIG. 5 is a cross sectional view of an internally finned catalyst tube 2 for use in the invention. A liquid cooling agent 1 is outside longitudinal finned steel tube 2, where the number of inner fins preferably is greater than 3.14 multiplied with the nominal inner tube diameter divided with the equivalent diameter of the catalyst pellet. The inner fins will create a void between the steel wall and the catalyst bed allowing the methanol condensate to flow down with less resistance. A fixed catalyst bed 3 is arranged inside the tube and a methanol condensate film 4 flows downwards between the inner tube wall and the catalyst bed 4.

Figure 6:
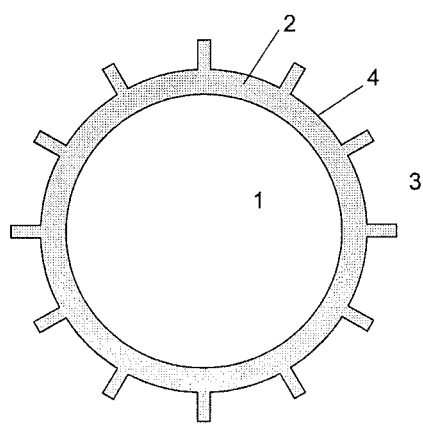

FIG. 6 is a cross sectional view of an externally finned cooling tube for use in the invention. A liquid cooling agent 1 is outside of a longitudinal finned steel tube 2, where the number of external fins preferably is greater than 3.14 multiplied with the nominal outer tube diameter divided with the equivalent diameter of the catalyst pellet. The outer fins will create a void between the steel wall and the catalyst bed allowing a methanol condensate film 4 to flow on the inner tube wall with less resistance.

Figure 7:
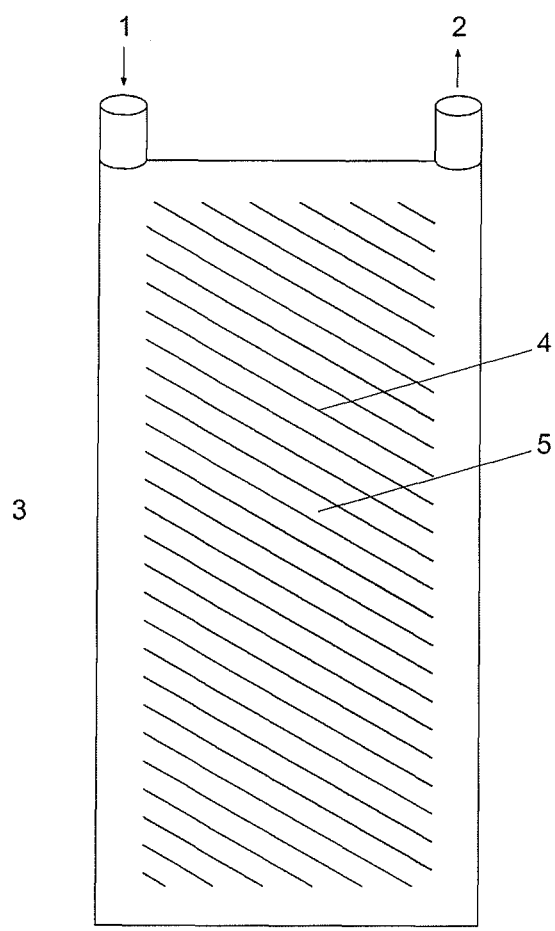

FIG. 7 is a corrugated plate heat exchanger for use as a cooling area according to the invention. A liquid cooling agent 1 is introduced through inlet 1a, which leaves the heat exchanger in gaseous form 2 through outlet 2a. A fixed catalyst bed 3 surrounds the plate exchanger. The heat exchanger is provided with a sinoidal corrugated surface 4 that provides void between the catalyst particles and the heat exchanger surface allowing condensed methanol 5 to flow on the surface with less resistance. The wavelength of the sinoidal corrugation is less than the equivalent diameter of the catalyst.

Figure 8:
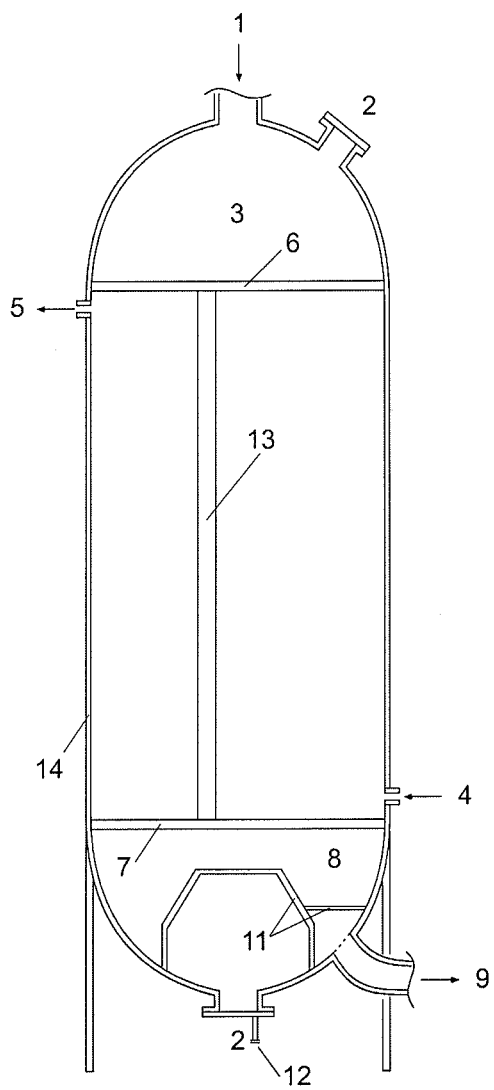

FIG. 8 shows a longitudinal view of a multi-tubular methanol reactor according to a specific embodiment of the invention. The reactor is provided in its pressure shell 14 with a synthesis gas inlet 1, a manhole 2, an inlet 4 for a liquid cooling agent, an outlet 5 for a liquid-vapour mixture of the cooling media, an outlet 9 for unconverted synthesis gas and liquid raw methanol and a liquid train 12. At top part 3 of the reactor an upper tube sheet 6, top part 3 can optionally be partially filled with a catalyst. In the bottom region of the reactor a lower tube sheet 7, 8 a support bed of inert spheres 8 and a perforated support grid 11 that holds the inert bed. A plurality of tubes 13 are filled with methanol catalyst, these tubes may each hold a liquid-stabilizing equipment as described above. The tubes are arranged in a triangular pitch. Methanol being formed inside the tubes condensates on inner wall of the tubes being cooled by the cooling agent and flows downwards to outlet 9.

FIG. 9 is a longitudinal view of a methanol reactor with a catalytic bed 8 and a tubular heat exchanger 11 arranged within the catalyst bed according to a specific embodiment of the invention. Methanol synthesis gas is introduced through inlet 1 and passed through catalyst bed 8. Liquid cooling agent is introduced via an inlet manifold 4 into tubular heat exchanger 11 and withdrawn in form of a vapour-liquid mixture through outlet manifold 5. At bottom of the reactor a perforated support grid 6 holds a support bed 9 of inert spheres. The major part of the catalysts is situated between heat exchanger 11 consisting of either a plurality of tubes, tubes with a liquid film stabilizer on the outer surface, longitudinal fined tubes or corrugated heat exchange plates. Methanol as it is formed within the catalyst bed is condensed on surface of heat exchanger 11 and is withdrawn in the liquid phase though outlet 10.

Figure 10:
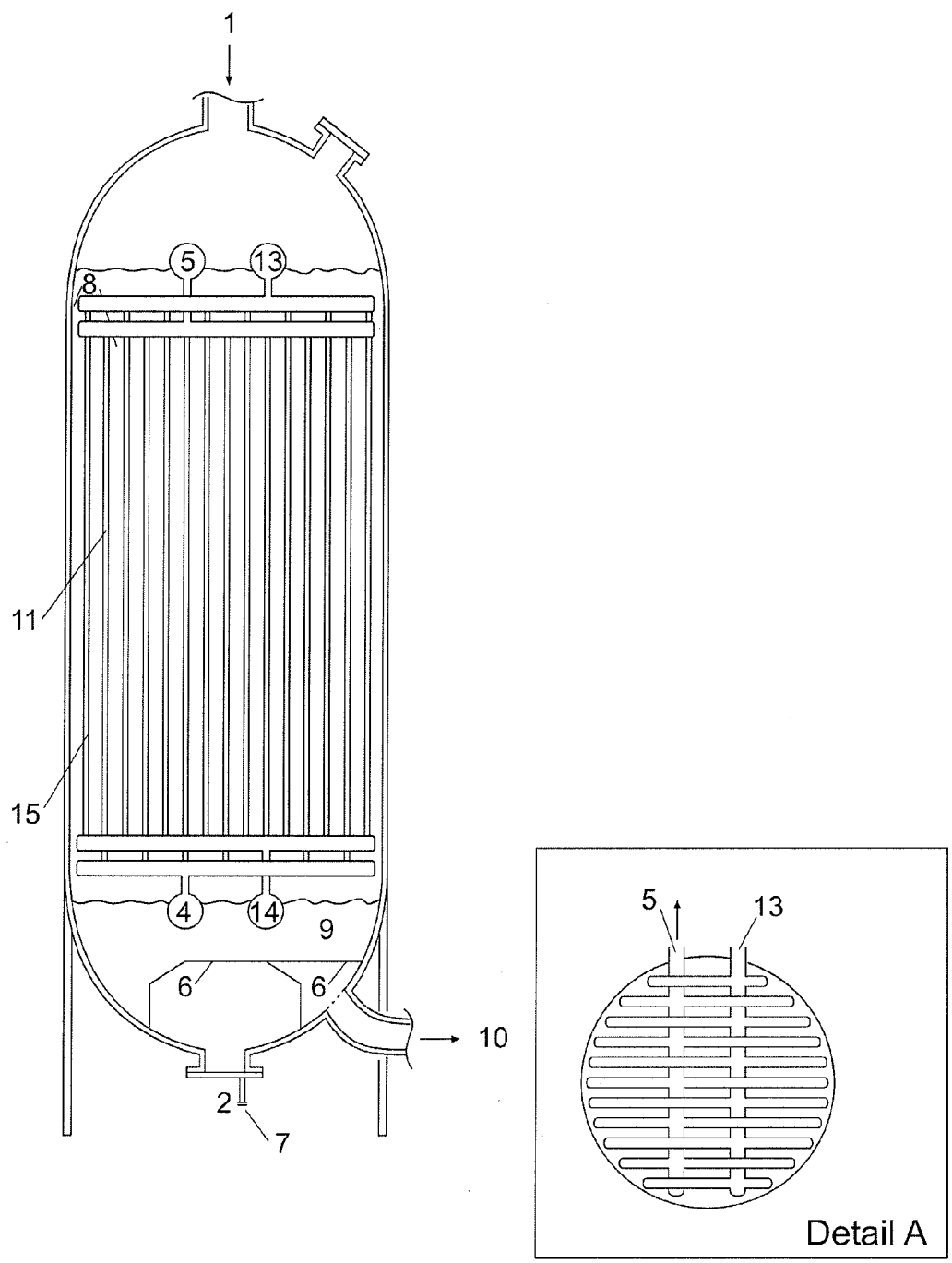

FIG. 10 is a longitudinal view of a methanol reactor being provided with a fixed bed of methanol catalyst 8 according to a specific embodiment of the invention. Within bed 8 is mounted a cooling surface in form of a tubular heat exchanger 11 and a heating surface in form of a tubular heat exchanger 15. At bottom of the reactor a perforated support grid 6 holds a support bed 9 of inert spheres. Methanol synthesis gas is introduced into bed 8 via inlet 1. A heating agent is introduced into heat exchanger 15 via inlet manifold 13 and withdrawn through outlet manifold 14. A liquid cooling agent is introduced into heat exchanger 11 via an inlet manifold 4 and is withdrawn through outlet manifold 5. Methanol being formed in bed 8 condensates on the cooling surface of heat exchanger 11 and is withdrawn from the reactor in the liquid phase through outlet 10. The cooling surface of heat exchanger 11 consists of either a plurality of tubes, tubes with a liquid film stabilizer on the outer surface, longitudinal fined tubes or corrugated heat exchange plates where the raw methanol condensates. Heat exchanger 15 maintains the temperature of the catalyst bed above the dew point of formed methanol and consists of either a plurality of tubes or heat exchange plates.

FIG. 11 is a sectional view of radial flow methanol reactor according to a specific embodiment of the invention. Methanol synthesis gas is introduced into the reactor via inlet 1. The synthesis gas is passed through catalyst bed 14 in radial direction from the periphery of the reactor through a cylindrical perforated cylinder 7 that holds the catalyst bed and allows the inlet synthesis gas to pass to a centre tube 6 being perforated where in contact with the catalyst to allow the residual synthesis gas and the liquid raw methanol being formed to be withdrawn through outlet 13. A cooling surface in form of a heat exchanger 9 consisting of either a plurality of tubes, tubes with a liquid film stabilizer on the outer surface, longitudinal fined tubes or corrugated heat exchange plates is arranged within catalyst bed 14. A liquid cooling agent is introduced into the heat exchanger through inlet 4 and withdrawn through outlet 5. The cooling agent is distributed to the heat exchanger by means of circular manifold 10 and collected at the outlet from the heat exchanger by outlet manifold 11.

Figure 12:
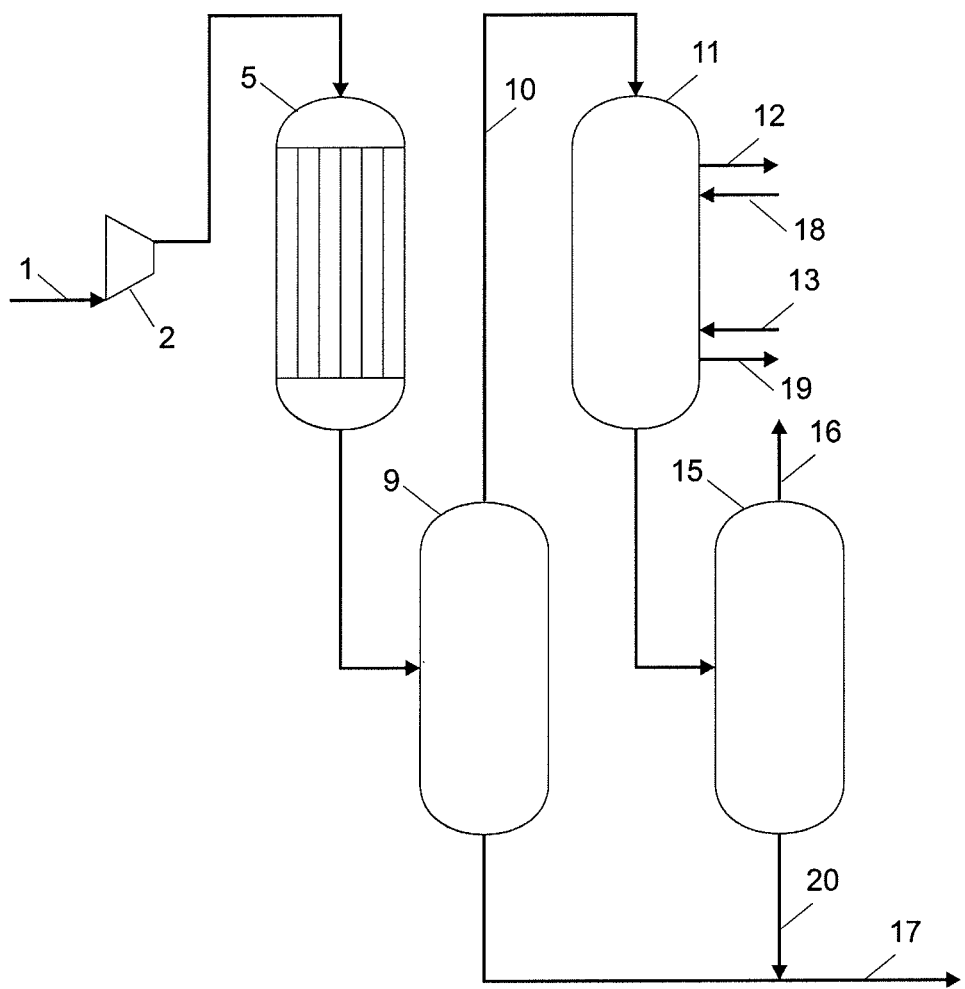

FIG. 12 shows a process flow diagram for the preparation of methanol in accordance with the invention. Methanol synthesis gas 1 is compressed synthesis gas compressor and passed to a conventional multi-tubular boiling water reactor 5 as typically employed in the industry today. The effluent from reactor 5 containing methanol and unconverted synthesis gas is passed to separator 9 and separated into a synthesis gas rich stream 10 and a methanol rich stream 17. Stream 10 is introduced into methanol reactor 11 being designed in accordance with the invention. A cooling agent with a boiling point between 60° C. and 170° C. is introduced into reactor 11 via inlet 13 and withdrawn from outlet 12. A heating agent is introduced through inlet 18 and withdrawn through outlet 19. The effluent from reactor 11 containing liquid methanol and unconverted synthesis gas is passed to a separator 15 and separated into a synthesis gas stream 16 and a liquid methanol stream 20, which is combined with the methanol stream from reactor 9 in line 17.

EXAMPLE 1

Reactor design and process conditions for a method and reactor of the above discussed type 1 are determined by means of the following equations based on predetermined values of:

P=12.55 MPa reactor pressure at synthesis gas inlet;

Synthesis gas composition at reactor inlet:

$Y(CH_3OH)$=0.255; $Y(H_2)$=0.438; $Y(CO)$=0.148; $Y(CO_2)$=0.075; $Y(H_2O)$=0.006

Equivalent diameter of the catalyst particles:

DEQ=0.006 m

With predetermined design values of TBW=130° C., Z=5, the following reactor design with an optimal condensation of methanol on the cooling surface inside the reactor can be determined as follows:

Since Z=VCAT/(ACOOL*DEQ) and Z and DEQ are known, VCAT/ACOOL can be calculated as:

VCAT/ACOOL=5*0.006 m=0.03 m

For a multi-tubular reactor of type 1, the ratio of VCAT/ACOOL is equal to ¼ of the inner diameter of the tube, giving an inner tube diameter of 0.12 m.

In order to keep the average liquid cooling agent temperature TBW at 130° C., pressurized boiler feed water at 5.0 MPa and 110° C. is used to cool the reactor, the cooling agent flow is adjusted in order to obtain a cooling agent outlet temperature of 150° C., giving an average cooling agent temperature of 130° C.

The invention claimed is:

1. A methanol reactor, comprising within a common shell a fixed bed of a methanol catalyst and cooling means adapted to indirectly cooling a reacting methanol synthesis gas with a cooling agent, wherein ratio (Z) of catalyst bulk volume to multiplication product of area of cooling surface of the cooling means with equivalent diameter of the catalyst (DEQ) is between 2.0 and 30, where the equivalent diameter of the catalyst is calculated by means of the following equation:

$DEQ_1$=(6*(volume of a particle of the methanol synthesis catalyst[m³]/3.14)$^{0.33}$ with catalyst particles of the same size and with catalyst particles of different size by means of the following equation:

$$DEQ_2=(\Sigma w(i)*(DEQ(i)^3))^{0.33},$$

where:

w(i) is the weight fraction of catalyst particles with an equivalent diameter of DEQ(i)[m].

2. A methanol reactor according to claim 1, further comprising heating means adapted to indirectly maintaining temperature of the methanol catalyst with a heating agent, wherein surface ratio of the surface of the heating means to the cooling means is between 0.3 and 3.0.

3. A methanol reactor according to claim 1, wherein the ratio Z is between 2 and 15.

4. A methanol reactor according to claim 1, further comprising internal film stabilizing equipment adjacent to surface of the cooling means.

* * * * *